(12) United States Patent
Janda

(10) Patent No.: US 10,792,272 B2
(45) Date of Patent: Oct. 6, 2020

(54) METHODS FOR TREATMENT OF CLOSTRIDIUM DIFFICILE INFECTIONS

(71) Applicant: The Scripps Research Institute, La Jolla, CA (US)

(72) Inventor: Kim D. Janda, La Jolla, CA (US)

(73) Assignee: THE SCRIPPS RESEARCH INSTITUTE, La Jolla, CA (US)

( * ) Notice: Subject to any disclaimer, the term of this patent is extended or adjusted under 35 U.S.C. 154(b) by 0 days.

(21) Appl. No.: 16/317,914

(22) PCT Filed: Jul. 14, 2017

(86) PCT No.: PCT/US2017/042056
§ 371 (c)(1),
(2) Date: Jan. 15, 2019

(87) PCT Pub. No.: WO2018/013890
PCT Pub. Date: Jan. 18, 2018

(65) Prior Publication Data
US 2019/0350891 A1    Nov. 21, 2019

Related U.S. Application Data

(60) Provisional application No. 62/362,675, filed on Jul. 15, 2016.

(51) Int. Cl.
| | | |
|---|---|---|
| *A61K 31/166* | (2006.01) | |
| *A61K 31/167* | (2006.01) | |
| *A61P 31/04* | (2006.01) | |
| *A61K 31/277* | (2006.01) | |

(52) U.S. Cl.
CPC .......... *A61K 31/277* (2013.01); *A61K 31/166* (2013.01); *A61K 31/167* (2013.01); *A61P 31/04* (2018.01)

(58) Field of Classification Search
None
See application file for complete search history.

(56) References Cited

U.S. PATENT DOCUMENTS 3,798,258 A * 3/1974 Patchett et al. ........ A61K 31/16
564/166

FOREIGN PATENT DOCUMENTS

| WO | WO-2016038035 A1 | 3/2016 | |
|---|---|---|---|
| WO | WO-2016193136 A1 * | 12/2016 | ........... A61K 31/609 |
| WO | WO-2018013890 A1 | 1/2018 | |

OTHER PUBLICATIONS

"International Application Serial No. PCT/US2017/042056, International Search Report dated Oct. 2, 2017", 2 pgs.
"International Application Serial No. PCT/US2017/042056, Written Opinion dated Oct. 2, 2017", 3 pgs.
Gooyit, Major, et al., "Reprofiled anthelmintics abate hypervirulent stationary-phase Clostridium difficile", Scientific Reports; vol. 6, Article No. 33642, (Sep. 16, 2016), 8 pgs.
Shah, Dhara, et al., "Clostridium difficile infection: update on emerging antibiotic treatment options and antibiotic resistance", NIH Public Access: Author Manuscript. Published in final edited form as: Expert Review of Anti-infective Therapy; vol. 8, Issue 5, (May 2010), 16 pgs.
"European Application Serial No. 17828511.0, Response filed Sep. 3, 2019 to Office Action dated Feb. 22, 2019", 17 pages.
"European Application Serial No. 17828511.0, Extended European Search Report dated Jan. 7, 2020", 8 pages.
Johnson, Alan P, "New antibiotics for selective treatment of gastrointestinal infection caused by Clostridium difficile", Expert Opinion on Therapeutic Patents, vol. 20, No. 10, (2010), pp. 1389-1399.
Macielag, M J, "Substituted Salicylanilides as Inhibitors of Two-Component Regulatory Systems in Bacteria", Journal of Medicinal Chemistry, vol. 41, No. 16, cited in the application, (Jan. 1, 1998), pp. 2939-2945.
Major, Gooyit, "Dual Protonophore-Chitinase Inhibitors Dramatically Affect O. volvulus Molting", Journal of Medicinal Chemistry, vol. 57, No. 13 cited in the application, (Jun. 20, 2014), pp. 5792-5799.
Pauk, Karel, "New derivatives of salicylamides: Preparation and antimicrobial activity against various bacterial species", Bioorganic and Medicinal Chemistry, vol. 21, No. 21 cited in the application, (Aug. 24, 2013), pp. 6574-6581.

* cited by examiner

*Primary Examiner* — Marcos L Sznaidman
*Assistant Examiner* — Rayna Rodriguez
(74) *Attorney, Agent, or Firm* — Schwegman Lundberg & Woessner, P.A.

(57) ABSTRACT

In this study, we capitalized on the antimicrobial property and low oral bioavailability of known salicylanilide anthelmintics (closantel, rafoxanide, niclosamide, oxyclozanide) to target the gut pathogen. The anthelmintics displayed excellent potency against *C. difficile* strains 630 and 4118 (with MIC values as low as 0.06-0.13 μg/mL for rafoxanide) via a membrane depolarization mechanism, interestingly, closantel, rafoxanide and compound 8 were bactericidal against logarithmic- and stationary-phase cultures of the BI/NAP1/027 strain 4118. Further evaluation of the salicylanilides showed their preferential activity against Gram-positive over Gram-negative bacteria. Moreover, the salicylanilides were non-hemolytic and were non-toxic to mammalian cell lines HepG2 and HEK 293T/17 within the range of their in vitro MICs and MBCs. The salicylanilide anthelmintics exhibit desirable bactericidal and pharmacokinetic properties and are amenable to repositioning as anti-*C. difficile* agents.

4 Claims, 3 Drawing Sheets

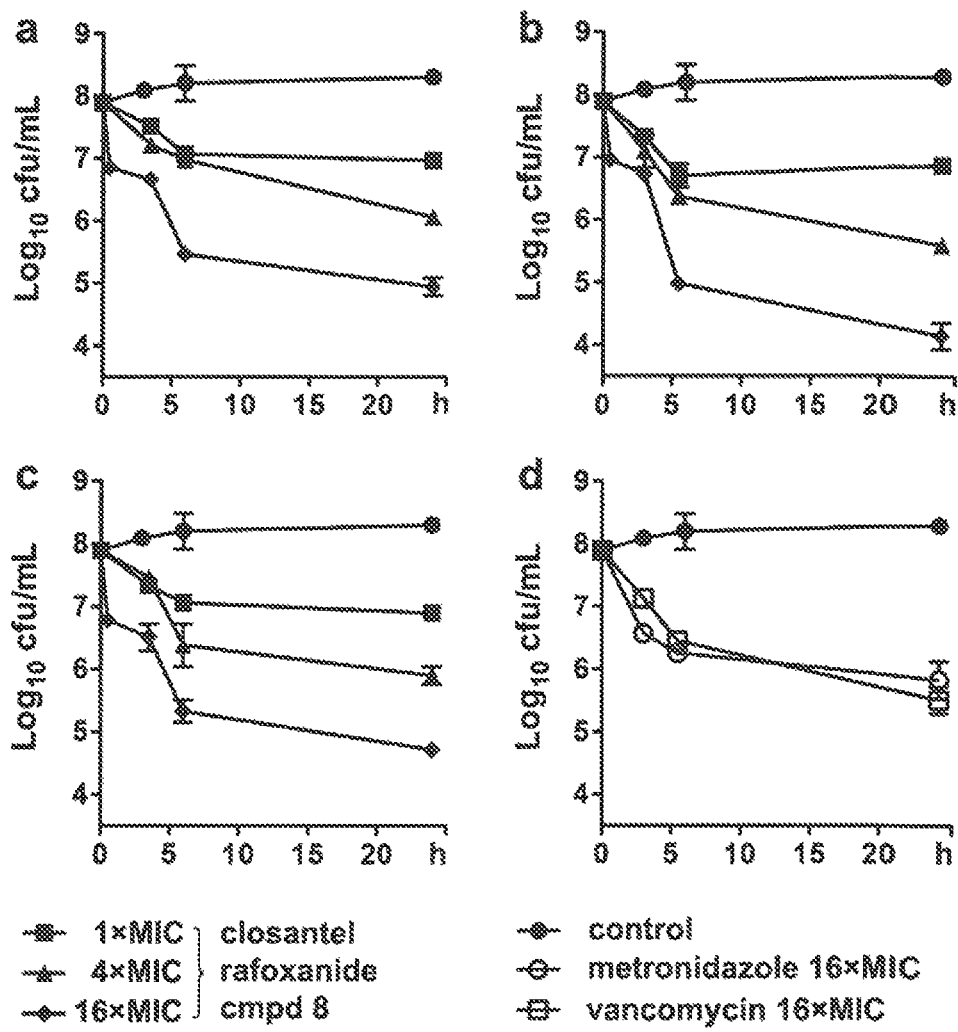

METHODS FOR TREATMENT OF *CLOSTRIDIUM DIFFICILE* INFECTIONS

CROSS-REFERENCE TO RELATED APPLICATIONS

This application is a national stage application filed under 35 U.S.C. § 371 from International Application Serial No. PCT/US2017/042056, filed on Jul. 14, 2017, and published as WO 2018/013890 on Jan. 18, 2018, which claims the benefit of priority to U.S. provisional application Ser. No. 62/362,675, filed on Jul. 15, 2016, the disclosures of which are incorporated herein by reference in their entireties.

BACKGROUND

*Clostridium difficile* infections (CDI) has plagued nearly half a million Americans that resulted in 29,300 deaths in 2011,[1] and the propensity of nosocomial CDI recurrence has been observed in up to 50% of patients.[2] The growing epidemic of CDI has been largely attributed to the emergence of the hypervirulent strain BI/NAP1/027,[3-5] coupled with the paucity of therapeutics that specifically target the gram-positive, spore-forming *bacillus* as well as, prevent the recrudescence of the disease. Although current treatment options (metronidazole and vancomycin) are still able to manage moderate cases of CDI, the escalating rates of fulminant and recurrent infections pose a significant threat that warrant immediate attention. Fidaxomicin is a non-absorbed oral macrocyclic antibiotic that was recently approved by the FDA for the treatment of CDI. It demonstrated similar rates of clinical cure as vancomycin[6,7] and significantly lowered the rate of recurrence of non-NAP1-associated infections[6]—a finding that is attributable to its high selectivity against *C. difficile*[8,9] and its ability to inhibit toxin and spore production in the offending pathogen.[10,11] However, there was no difference in outcomes observed for patients that were infected with the hypervirulent BI/NAP1/027 strain.[6] Although resistance is not widespread as of yet, *C. difficile* strains with reduced susceptibility to metronidazole, vancomycin or fidaxomicin have already been noted.[12-14]

The persistence of CDI is alarming in its breadth and points to the pressing need to identify effective treatment options. As a result, the scientific community has risen to the challenge of developing alternative small molecule and biotherapeutic strategies to combat the infectious malady.[15] It is evident that anti-*difficile* agents with low oral bioavailability (to localize the drug at the site of infection) and a narrow antimicrobial spectrum (to minimize collateral damage to the resident gastrointestinal microbiome) are preferable. Hypervirulent *C. difficile* isolates have been shown to produce robust amounts of lethal toxins (TcdA and TcdB) and spores primarily during the stationary phase of growth.[4] This sets an impediment because quiescent stationary-phase cells are especially resilient to antimicrobial chemotherapy.[16] An emerging strategy to combat refractory dormant *C. difficile* is to target the vulnerability of its membrane. The clinical relevance of such concept lies in the essentiality of the microbial membrane in both metabolizing and non-growing cells, and the associated multifactorial mechanism of action that could limit the likelihood of bacteria to develop resistance.[17] Indeed, membrane-active agents have demonstrated potential in eliminating quiescent *C. difficile* cells, which subsequently led to a substantial decrease in toxin production and sporulation.[16,18,19]

The salicylanilides have been reported to exhibit antimicrobial properties[20,21] albeit they are chiefly exploited as antiparasitic agents. Closantel (1), rafoxanide (2), niclosamide (3) and oxyclozanide (4) represent four of the widely used salicylanilide anthelmintics (FIG. 1).

Niclosamide is an FDA-approved drug for the treatment of tapeworm infections, while the other three are marketed as veterinary drugs for liver fluke/roundworm infections in ruminants.[22] The exact antibacterial mode of action of salicylanilides is not well defined but is thought to involve dissipation of the (trans)membrane potential or the proton motive force (pmf). The pmf modulates the spatial organization of morphogenetic proteins[23] as well as ATP homeostasis that is vital for bacterial survival.[24] These functions of the pmf offer an explanation for the effects observed with certain membrane-active compounds, albeit depletion of which does not always result to cell death in many bacterial pathogens.[25] The potential use of salicylanilides as antimicrobials has drawn considerable interest as exemplified by recent studies demonstrating the anti-staphylococcal properties of closantel, niclosamide and oxyclozanide.[26,27]

A limiting aspect is the low oral bioavailability of salicylanilides, which may render them ineffective in treating systemic infections. For instance, niclosamide was found to be only partially absorbed from the GI tract (with a maximal serum concentration ranging from 0.25 to 6 µg/mL after oral administration to human volunteers) and was also poorly distributed to tissues.[28] Closantel, rafoxanide and oxyclozanide exhibited similar pharmacokinetic (PK) attributes and were minimally metabolized and mostly excreted unchanged (up to ~90% for closantel) in the feces in ruminants.[22]

SUMMARY

The invention provides, in various embodiments, a method of treatment of a *Clostridium difficile* infection in a mammal, comprising administering to the mammal an effective dose of a compound of formula (I)

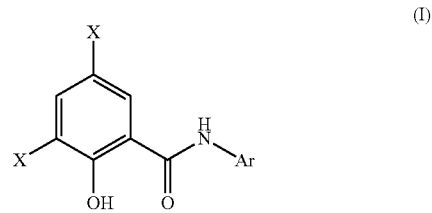

wherein X is halo or H, provided at least one X is halo, wherein the ring bearing X is optionally further substituted with halo;

wherein Ar is phenyl, benzyl, phenethyl, biphenyl, benzhydryl, phenoxyphenyl, naphthyl, or indanyl, any of which can be unsubstituted or independently substituted with one or more halo, (C1-C4)alkyl, cyano, or nitro groups.

More specifically, X can be chloro or iodo. More specifically, Ar can be phenyl, phenethyl, or phenoxyphenyl, any of which can be substituted with halo or (C1-C4)alkyl or both.

For instance, the compound of formula (I) can be any one of compounds closantel (1), rafoxanide (2), niclosanide (3), oxyclozanide (4), or of any one of a compound of formula (5a), (5e), (5f), (5g), (6a), (7a), (7b), (7c), (7d), (7e), (7f), (7g), (7h), (7i), or (8).

BRIEF DESCRIPTION OF THE FIGURES

FIG. 3. Time-kill kinetics against stationary-phase cultures of BI/NAP1/027 strain 4118. Various concentrations of A) closantel, B) rafoxanide, C) compound 8, and D) metronidazole or vancomycin are shown. Data plotted as mean $\log_{10}$ cfu/mL.±s.d. versus time in h (n=2).

DETAILED DESCRIPTION

Prolonged use of broad-spectrum antibiotics disrupts the indigenous gut microbiota, which consequently enables toxigenic *Clostridium difficile* species to proliferate and cause infection. The burden of *C. difficile* infections was exacerbated with the outbreak of hypervirulent BI/NAP1/027 strains that produce copious amounts of enterotoxins and spores. In recent past, membrane-active agents have generated a surge of interest due to their bactericidal property with a low propensity for resistance.

We show that the salicylanilide derivatives efficiently inhibited the growth of *C. difficile* via membrane depolarization, and more importantly, killed both logarithmic- and stationary-phase cells in a concentration-dependent manner. The bactericidal property against quiescent *C. difficile* could in principle lower the production of toxins and spores, which would in turn mitigate disease severity and recurrence.

Figure 1:
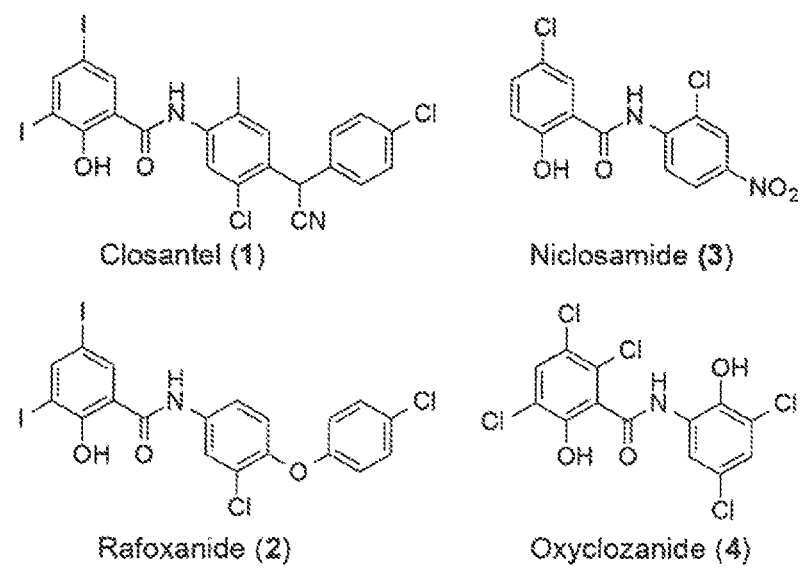
FIG. 1. Structures of salicylanilide anthelmintics useful for practice of a method of the invention.
Figure 2:
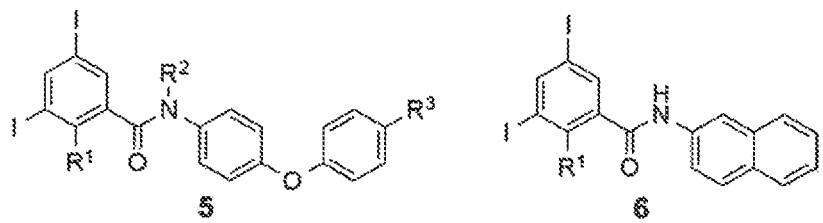
FIG. 2. Structures of salicylanilide analogues useful for practice of a method of the invention.
Figure 2:
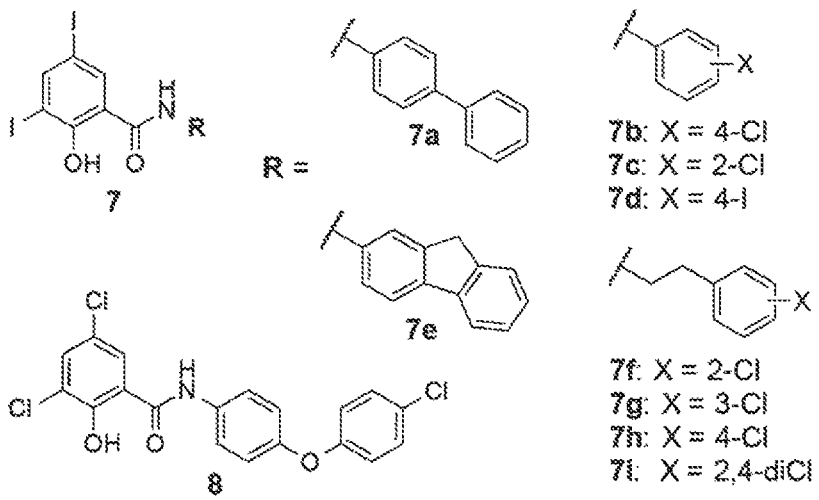

We initially tested the known anthelmintics closantel, rafoxanide, niclosamide and oxyclozanide for their activities against *C. difficile* strains 630 (CD630, ATCC BAA-1382) and 4118 (CD4118, ATCC BAA-1870). CD630 is a virulent, multidrug-resistant strain whose genome has been completely sequenced,[29] while CD4118 is a BI/NAP1/027 hypervirulent pathogen. All four salicylanilides displayed excellent potency with MIC values as low as 0.06-0.13 µg/mL for rafoxanide (Table 1). In comparison, metronidazole had an MIC value of 0.25 µg/mL, whereas that of vancomycin was significantly higher at 1-2 µg/mL (Table 1). In order to ascertain that the observed activity of the salicylanilides occurs through dissipation of the bacterial membrane potential, we prepared analogues 5 and 6 (FIG. 2) as previously described,[39] and evaluated their growth inhibitory activity against CD630 and CD4118. We have earlier delineated the structural features that are necessary for protonophoric activity of salicylanilides, requiring both a dissociable phenolic OH group and an amide proton that forms an intramolecular hydrogen bond to maintain hydrophobicity and stabilize the anionic form of the molecule.[30] The MIC values that were determined for 5 and 6 are consistent with a membrane depolarization mechanism as the compounds devoid of protonophoric activity [i.e. analogues that lack either the weakly acidic OH (5b, 5c, 5h, 5i, 6b and 6c) or the amide proton (5d)] were inactive, whereas protonophores 5a, 5e, 5f, 5g, and 6a exhibited high in vitro potency against CD630 and CD4118 (Table 1). Encouraged by these results, we explored several other derivatives, which harbor the diidosalicylate moiety coupled to varying substituents including biphenyl (7a), halogenated mono-aryl rings (7b-d), a fused-ring fluorenyl core (7e) and the more flexible ethylbenzenes (7f-i). Compounds 7a-i demonstrated low MIC values (≤2 µg/mL), except for the ortho-chloro analogue 7c, which showed reduced activity against CD630 and CD4118 (MIC=8 µg/mL). Replacement of the diiodosalicylate with its dichloro congener (compound 8) resulted in a 4-fold enhancement of potency relative to 5g and metronidazole, and ~32-fold improvement of activity over vancomycin (Table 1).

TABLE 1

MIC against *Clostridium difficile* strains 630 and 4118.

| Cmpd | MIC | |
|---|---|---|
| | *C. difficile* 630 | *C. difficile* 4118 |
| Closantel | 0.13 | 0.25 |
| Rafoxanide | 0.06 | 0.13 |
| Niclosamide | 1 | 4 |
| Oxyclozanide | 0.5 | 1 |
| 5a | 0.5 | 1 |
| 5b | >32 | >32 |
| 5c | >32 | >32 |
| 5d | >32 | >32 |
| 5e | 0.13 | 0.13 |
| 5f | 0.13 | 0.25 |
| 5g | 0.13 | 0.25 |
| 5h | >32 | >32 |
| 5i | >32 | >32 |
| 6a | 0.5 | 0.5 |
| 6b | >32 | >32 |
| 6c | >32 | >32 |
| 7a | 0.5 | 1 |
| 7b | 0.25 | 0.5 |
| 7c | 8 | 8 |
| 7d | 0.13 | 0.25 |
| 7e | 0.25 | 0.5 |
| 7f | 2 | 2 |
| 7g | 1 | 1 |
| 7h | 0.25 | 0.5 |
| 7i | 0.25 | 0.5 |
| 8 | ≤0.03 | 0.06 |
| Metronidazole | 0.25 | 0.25 |
| Vancomycin | 1 | 2 |

All minimum inhibitory concentration (MIC) values are expressed in µg/mL.

The foregoing observations led us to probe other ionophores such as tropolones and β-carbolines as well as other structurally related compounds lacking the salicylanilide moiety; however, none of these were found to be active against CD630 and CD4118 (MIC>32 µg/mL).

Salicylanilides are Bactericidal Against Logarithmic- and Stationary-Phase Cultures The superb growth inhibitory potency exhibited by the salicylanilides spurred us to further investigate their bactericidal activities against *C. difficile*. Although ionophores are known to dissipate the pmf that is crucial for bacterial energy metabolism, they do not always display bactericidal activity.[25,27] We were particularly interested in determining the cidal effect on stationary-phase *C. difficile* cells, because these quiescent cells are the primary producer of toxins and spores that contribute to the severity and recurrence of CDI.[4] We selected the more potent compounds (closantel, rafoxanide and 8) and assayed them for minimum bactericidal concentration (MBC, defined as the lowest concentration of the antibacterial agent required to kill ≥99.9% of the initial inoculum) against growing and non-growing cells of the BI/NAP1/027 pathogen CD4118. As shown in Table 2, all three compounds displayed bactericidal activities against both logarithmic- and stationary-phase cells of CD4118 at concentrations close to their MIC values. The $MBC_{log}$ values of the protonophores were determined to be 0.25-2 µg/mL (~4 to 8-fold greater than their respective MIC values). Significantly, the salicylanilides retained bactericidal activities against dormant stationary-phase *C. difficile* cells, in stark contrast to metronidazole and vancomycin, which did not result in ≥3-log reduction of CD4118 cells at 32 µg/mL (Table 2).

Next, we determined the time-kill kinetics of closantel, rafoxanide and 8 (at 1×, 4×, and 18× their respective MICs) against stationary-phase cultures of CD4118. As depicted in FIG. 3, all three salicylanilides showed a concentration-dependent mode of killing of the quiescent cells. At 16× the MIC of each protonophore, rafoxanide (at 2 µg/mL) eradicated >99.9% of viable cells in 6 h (FIG. 3b), while closantel (at 4 µg/mL) and compound 8 (at 1 µg/mL) achieved a similar potency in 24 h (FIGS. 3a and 3c). At four-fold lower concentrations (i.e. 4×MIC), rafoxanide caused a 2.7-log decrease in the number of CFUs in 24 h, comparable to those of closantel and 8, which reduced bacterial cell viability by 2.2- and 2.4-log, respectively. In comparison, neither metronidazole (at 4 µg/mL) nor vancomycin (at 32 µg/mL) reached 3-log killing of CD4118 stationary-phase cells, even at 16× their respective MIC values (FIG. 3d). The rapid bactericidal property demonstrated by closantel, rafoxanide and 8 is a significant finding because quiescent *C. difficile* cells are notoriously recalcitrant to antibiotic-mediated killing.[16] We surmise that the cidal effect of such protonophores on stationary-phase *C. difficile* cells would ameliorate the effect of toxin production and spore formation, similar to what was observed with other membrane-active compounds.[16]

TABLE 2

In vitro activity against *Clostridium difficile* strain 4118.

| Cmpd | MIC | $MBC_{log}$ | $MBC_{stat}$ |
|---|---|---|---|
| Closantel | 0.25 | 2 | 4 |
| Rafoxanide | 0.13 | 0.5 | 1 |
| 8 | 0.06 | 0.25 | 1 |
| Metronidazole | 0.25 | >32 | >32 |
| Vancomycin | 2 | 8 | >32 |

Abbreviations: MIC, minimum inhibitory concentration; $MBC_{log}$, minimum bactericidal concentration for logarithmic-phase cells; $MBC_{stat}$, minimum bactericidal concentration for stationary-phase cells. All MIC and MBC values are expressed in µg/mL.

Salicylanilides Mainly Target Gram-Positive Bacteria

In an effort to assess the antibacterial spectrum of protonophores, we evaluated representative compounds (closantel, rafoxanide, 6a, 7b, 8) against a panel of aerobic and anaerobic organisms. All five agents were generally more selective against Gram-positive bacteria, displaying high potency against *B. subtilis* ATCC 6051, *S. aureus* RN4220 and *S. epidermidis* 1457 (MIC≤0.25 µg/mL) and modest activity against other anaerobic clostridial species *C. sporogenes* ATCC 15579 and *C. clostridioforme* ATCC 25537 (MIC=1-16 µg/mL). By comparison, the compounds were ineffective against aerobic Gram-negative bacteria (MIC 32 µg/mL against *A. baumannii* M2 and *P. aeruginosa* PAO1) and had modest MIC values of ≥4 µg/mL against gut commensals *B. thetaiotaomicron* ATCC 29148, *P. distasonis* ATCC 8503 and *P. nigrescens* ATCC 33563. These results are consistent with those of niclosamide and oxyclozanide, which were shown to primarily target Gram-positive bacteria.[27] Compound 5i, which does not possess protonophoric activity,[30] lacked antibacterial activity whereas metronidazole and vancomycin mainly targeted anaerobic bacteria and Gram-positive organisms, respectively. The complex multilayered cell envelopes of Gram-negative organisms impose a permeability barrier to microbial agents and most likely account for the diminished potency observed for the salicylanilide molecules. Of note, rafoxanide and 8 had MIC values of ≤0.13 µg/mL for *C. difficile*, which rendered ≥32-fold selectivity over the Gram-negative gut commensals that were tested.

In Vitro Cytotoxicity and Hemolytic Activity of Salicylanilides

Although the salicylanilides have been used extensively in veterinary medicine, there is little information available concerning their biological effects on humans, except for niclosamide, which is FDA-approved for treatment of intestinal cestode infections. In order to gauge potential cytotoxicity of the salicylanilides, hemolysis using sheep erythrocytes and MTS[33] assay using two human cell lines (liver carcinoma HepG2 and embryonic kidney HEK 293T/17) were performed. A significant finding was that the salicylanilides (closantel, rafoxanide, niclosamide, oxyclozanide and compound 8) did not cause rupture of red blood cells when tested at 32 µg/mL. However, treatment of human cell lines with niclosamide led to a significant decrease in viability even at a low concentration of 0.125 µg/mL. Despite its high in vitro cytotoxicity, niclosamide is considered a "safe drug" because of its minimal absorption from the GI tract and high plasma protein binding,[28] thus sparing the host cells from its uncoupling property. An intriguing observation was the comparably lower in vitro toxicities of compound 8 and the veterinary drugs (closantel, rafoxanide, oxyclozanide) toward HepG2 and HEK 293T/17. Both closantel and rafoxanide had no apparent effect on mammalian cell viability even at a concentration of 8 µg/mL, which is ≥32-fold higher than their corresponding MIC values against *C. difficile* (Table 1). These results do not guarantee drug safety (relative to niclosamide) but nevertheless indicate the potential for repositioning of the veterinary anthelmintics as human drugs.

A common cause of antibiotic failure is the inadequate penetration of the target infection site. In the case of CDI, it is imperative that the active drug achieves therapeutic levels in the colon to repress or eliminate the outgrowth of toxigenic *C. difficile*. This places the salicylanilide anthelmintics at a definite advantage; their low oral bioavailability and high fecal excretion (as observed in ruminants and humans)[22,28] would in theory result in adequate gut concentrations necessary to disarm the target pathogen. A substantial feature of the salicylanilides (as we have shown for closantel, rafoxanide and 8) is their bactericidal activity against stationary-phase cultures of hypervirulent *C. difficile* a property that is not exhibited by many antibiotics including metronidazole and vancomycin.[16] Killing of dormant and hypervirulent *C. difficile* could likely suppress toxin production and inhibit sporulation, which in principle would lead to an improved sustained response and reduced recurrence rate. The clinical potential of membrane-active agents is demonstrated by daptomycin and telavancin, which function through permeabilization/depolarization of bacterial membranes and are FDA-approved to treat complicated skin and skin structure infections.[34,35] Our results exemplify notable attributes of the salicylanilide anthelmintics and demonstrate their potential for repurposing as anti-*Clostridium difficile* agents. Work is ongoing in our laboratory to exploit the salicylanilides as alternative therapies to combat CDI.

DOCUMENTS CITED

1 Lessa, F. C. et al. Burden of *Clostridium difficile* infection in the United States. *N. Engl. J. Med.* 372, 825-834, (2015).
2 Aslam, S., Hamill, R. J. & Masher, D. M. Treatment of *Clostridium difficile*-associated disease: old therapies and new strategies. *Lancet Infect. Dis.* 5, 549-557, (2005).

3 Loo, V. G. et al. A predominantly clonal multi-institutional outbreak of *Clostridium difficile*-associated diarrhea with high morbidity and mortality. *N. Engl. J. Med.* 353, 2442-2449, (2005).

4 Merrigan, M. et al. Human hypervirulent *Clostridium difficile* strains exhibit increased sporulation as well as robust toxin production. *J. Bacteriol.* 192, 4904-4911, (2010).

5 Kelly, C. P. & LaMont, J. T. *Clostridium difficile*—more difficult than ever. *N. Engl. J. Med.* 359, 1932-1940; (2008).

6 Louie, T. J. et al. Fidaxomicin versus vancomycin for *Clostridium difficile* infection. *N. Engl. J. Med.* 364, 422-431, (2011).

7 Cornely, O. A., Miller, M. A., Louie, T. J., Crook, D. W. & Gorbach, S. L. Treatment of first recurrence of *Clostridium difficile* infection: fidaxomicin versus vancomycin. *Clin. Infect. Dis.* 55 Suppl 2, S154-161, (2012).

8 Louie, T. J., Emery, J., Krulicki, W., Byrne, B. & Mah, M. OPT-80 eliminates *Clostridium difficile* and is sparing of *Bacteroides* species during treatment of *C. difficile* infection. *Antimicrob. Agents Chemother.* 53, 261-263, (2009).

9 Credito K. L. & Appelbaum; P. C. Activity of OPT-80, a novel macrocycle, compared with those of eight other agents against selected anaerobic species. *Antimicrob. Agents Chemother.* 48, 4430-4434, (2004).

10 Babakhani, F. et al. Fidaxomicin inhibits spore production in *Clostridium difficile. Clin. Infect. Dis.* 55 Suppl 2, S162-169, (2012).

11 Babakhani, F. et al. Fidaxomicin inhibits toxin production in *Clostridium difficile. J. Antimicrob. Chemother.* 68, 515-522, (2013).

12 Pelaez, T. et al. Metronidazole resistance in *Clostridium difficile* is heterogeneous. *J. Clin. Microbial.* 46, 3028-3032; (2008).

13 Snydman, D. R., Jacobus, N. V. & McDermott, L. A. Activity of a novel cyclic lipopeptide, CB-183,315, against resistant *Clostridium difficile* and other Gram-positive aerobic and anaerobic intestinal pathogens. *Antimicrob. Agents Chemother.* 56, 3448-3452, (2012).

14 Goldstein, E. J. et al. Comparative susceptibilities to fidaxomicin (OPT-80) of isolates collected at baseline, recurrence, and failure from patients in two phase III trials of fidaxomicin against *Clostridium difficile* infection. *Antimicrob. Agents Chemother.* 55, 5194-5199, (2011).

15 Jarrad, A. M., Karoli, Blaskovich, M. A., Lyras, D. & Cooper, M. A. *Clostridium difficile* drug pipeline: challenges in discovery and development of new agents. *J. Med. Chem.* 58, 5164-5185, (2015).

16 Wu, X., Cherian, P. T., Lee, R. E. & Hurdle, J. G. The membrane as a target for controlling hypervirulent *Clostridium difficile* infections. *J. Antimicrob. Chemother.* 68, 806-815, (2013).

17 Hurdle, J. G., O'Neill, A. J., Chopra, I. & Lee, R. E. Targeting bacterial membrane function: an underexploited mechanism for treating persistent infections. *Nat. Rev. Microbial.* 9, 62-75, (2011).

18 Bouillaut, L. et al. Effects of surotomycin on *Clostridium difficile* viability and toxin production in vitro. *Antimicrob. Agents Chemother.* 59, 4199-4205, (2015).

19 Hurdle, J. G., Heathcott, A. E., Yang, L., Yan, B. & Lee, R. E. Reutericyclin and related analogues kill stationary phase *Clostridium difficile* at achievable colonic concentrations. *J. Antimicrob. Chemother.* 66, 1773-1776, (2011).

20 Macielag, M. J. et al. Substituted salicylanilides as inhibitors of two-component regulatory systems in bacteria. *J. Med. Chem.* 41, 2939-2945, (1998).

21 Pauk, K. et al. New derivatives of salicylamides: Preparation and antimicrobial activity against various bacterial species. *Bioorg. Med. Chem.* 21, 6574-6581, (2013).

22 Swan, G. E. The pharmacology of halogenated salicylanilides and their anthelmintic use in animals. *J. S. Afr. Vet. Assoc.* 70, 61-70 (1999).

23 Strahl, H. & Hamoen, L. W. Membrane potential is important for bacterial cell division. *Proc. Natl. Acad. Sci. U.S.A* 107, 12281-12286, (2010).

24 Rao, S. P., Alonso, S., Rand, L., Dick, T. & Pethe, K. The protonmotive force is required for maintaining ATP homeostasis and viability of hypoxic, nonreplicating *Mycobacterium tuberculosis. Proc. Natl. Acad. Sci. U.S.A* 105, 11945-11950, (2008).

25 Tempelaars, M. H., Rodrigues, S. & Abee, T. Comparative analysis of antimicrobial activities of valinomycin and cereulide, the *Bacillus cereus* emetic toxin. *Appl. Environ. Microbial.* 77, 2755-2762, (2011).

26 Rajamuthiah, R. et al. Whole animal automated platform for drug discovery against multi-drug resistant *Staphylococcus aureus. PLoS One* 9, e89189, (2014).

27 Rajamuthiah, R. et al. Repurposing salicylanilide anthelmintic drugs to combat drug resistant *Staphylococcus aureus. PLoS One* 10, e0124595, (2015).

28 Andrews, P., Thyssen, J. & Lorke, D. The biology and toxicology of molluscicides, Bayluscide. *Phamacol. Ther.* 19, 245-295 (1983).

29 Riedel, T. et al. Genome resequencing of the virulent and multidrug-resistant reference strain *Clostridium difficile* 630. *Genome Announc.* 3, (2015).

30 Gooyit, M., Tricoche, N., Lustigman, S. & Janda, K. D. Dual protonophore-chitinase inhibitors dramatically affect *O. volvulus* molting. *J. Med. Chem.* 57, 5792-5799, (2014).

31 Gooyit, M. et al. *Onchocerca volvulus* molting inhibitors identified through scaffold hopping. *ACS Infect. Dis.* 1, 198-202 (2015).

32 Gooyit, M., Tricoche, N., Javor, S., Lustigman, S. & Janda, K. D. Exploiting the polypharmacology of 3-carbolines to disrupt *O. volvulus* molting. *ACS Med. Chem. Lett.* 6, 339-343, (2015).

33 Malich, G., Markovic, B. & Winder, C. The sensitivity and specificity of the MTS tetrazolium assay for detecting the in vitro cytotoxicity of 20 chemicals using human cell lines. *Toxicology* 124, 179-192 (1997).

34 Hawkey, P. M. Pre-clinical experience with daptomycin. *J. Antimicrob. Chemother.* 62 Suppl 3, iii7-14, (2008).

35 Zhanel, G. G. et al. New lipoglycopeptides: a comparative review of dalbavancin, oritavancin and telavancin. *Drugs* 70, 859-886, (2010).

All patents and publications referred to herein are incorporated by reference herein to the same extent as if each individual publication was specifically and individually indicated to be incorporated by reference in its entirety.

EXAMPLES

Bacterial Strains.

*Clostridium difficile* 630 (ATCC® BAA-1382-FZ™), *Clostridium difficile* 4118 (ATCC® BAA-1870™), *Clostridium sporagenes* (ATCC® 15579™), *Clostridium clostridioforme* (ATCC® 25537™), *Bacteroides* thetaiotaomicron (ATCC® 29148™, *Parabacteroides distasonis* (ATCC® 8503™) *Prevotella nigrescens* (ATCC®

33563™), and *Bacillus subtilis* (ATCC® 6051™) were purchased from ATCC (Manassas, Va., USA). *Pseudomonas aeruginosa* PAO1 was provided by Dr. Kendra Rumbaugh.

Bacterial Culture.

*Clostridium* species were routinely cultured either on blood agar base II plates with 5% sheep blood (Teknova), or in brain-heart infusion broth/agar plates supplemented with 0.5% yeast extract (BHIS) containing 0.03% L-cysteine. *Bacteroides thetaiotaomicron, Parabacteroides distasonis,* and *Prevotella nigrescens* were grown on *Brucella* broth/agar plates supplemented with hemin (5 µg/mL), vitamin $K_1$ (1 µg/mL) and 5% lysed horse blood. Anaerobic bacterial culture was performed in an anaerobic cabinet (Coy Lab Products) at 37° C. in a reducing anaerobic atmosphere (8% $H_2$, 8% $CO_2$, 84% $N_2$). All broths and 96-well plates were pre-reduced (incubated anaerobically overnight) prior to use for anaerobic culture. Aerobic bacteria were routinely cultured on Mueller-Hinton broth/agar plates.

Determination of Minimum Inhibitory Concentration (MIC).

All MICs were determined in 96-well plates using the broth microdilution method. Two-fold serial dilutions of test compounds were inoculated with ~5×10$^5$ cfu/mL bacteria. MIC was recorded as the lowest concentration of the test compound that inhibited visible bacterial growth after 20-24 h of incubation at 37° C. MIC assays were performed in duplicate.

Determination of Minimum Bactericidal Concentration (MBC).

*Clostridium difficile* strain 4118 was grown to $OD_{600}$~0.4-0.5 (logarithmic phase) or for 24 h (stationary phase), and thereafter added to two-fold serial dilutions of test compounds. Cultures were incubated for 20-24 h at 37° C., and then viable counts were enumerated on BHIS agar plates. The MBC was determined as the lowest concentration of the test compound that resulted in 3-log reduction of the initial cell inoculum. MBC measurements were performed in duplicate.

Time-Kill Kinetics Assay.

Stationary phase cultures of *Clostridium difficile* strain 4118 were treated with closantel, rafoxanide, compound 8 at 1×, 4×, 16×MIC or with metronidazole and vancomycin at 16×MIC. At various time points, sample aliquots were taken and determined for bacterial viability on BHIS agar plates. Kinetic experiments were performed in duplicate.

In Vitro Cytotoxicity Assay.

Cell lines Hep G2 [HEPG2] (ATCC® HB8065™) and 293T/17 [HEK 293T/17] (ATCC® CRL-11268™) were purchased from ATCC and cultured according to manufacturer's instructions. HEPG2 or HEK 2931/17 cells were plated in 96-well plates, and incubated at 37° C. in a 5% $CO_2$ humidifying chamber for 24 h. Cells were then treated with test compounds at varying concentrations, and an MTS assay was performed at 16-h post-incubation at 37° C. in a 5% $CO_2$ humidifying chamber, using the CellTiter 96 aqueous non-radioactive cell proliferation assay kit (Promega, Madison, Wis., USA) per manufacturer's instructions. MTS assays were performed in duplicate.

Hemolysis Assay.

Sheep red blood cells (Innovative Research, Novi, Mich., USA) were washed three times with PBS pH 7.4. A 3% cell suspension in PBS (100 µL) was added to test compounds in PBS (100 µL), and then incubated at 37° C. for 1 h. The plate was centrifuged at 500×g for 10 min, and supernatants (100 µL) were transferred to a clean 96-well plate. Hemolysis was determined by measuring absorbance at 540 nm, with 1% Triton X-100 as the positive control and 0.5% DMSO in PBS as the negative control. Hemolysis assays were performed in triplicate.

Tables 3 and 4 provide an indication of the bioactivity of compounds (5i), (6a), (7b), and (8) versus a selection of aerobic and anaerobic bacteria, respectively.

TABLE 3

In vitro activity against select aerobic bacteria

| strain | $MIC^a$ (µg/mL) | | | | | | | |
|---|---|---|---|---|---|---|---|---|
| | Closantel | Rafoxanide | 5i | 6a | 7b | 8 | metronidazole | vancomycin |
| *B. subtilis* ATCC 6051 | ≤0.03 | ≤0.03 | >32 | 0.06 | 0.06 | ≤0.03 | >32 | 0.13 |
| *S. aureus* RN4220 | 0.25 | 0.25 | >32 | 0.25 | 0.06 | 0.13 | >32 | 1 |
| *S. epidermidis* 1457 | ≤0.03 | ≤0.03 | >32 | 0.06 | ≤0.03 | ≤0.03 | >32 | 2 |
| *A. baumannii* M2 | >32 | >32 | >32 | >32 | 32 | 32 | >32 | >32 |
| *P. aeruginosa* PAO1 | >32 | >32 | >32 | >32 | >32 | >32 | >32 | >32 |

$^a$Performed in duplicate. For clarity, MIC values against Gram-positive and Gram-negative bacteria are shown in blue and red, respectively.

TABLE 4

In vitro activity against select anaerobic bacteria

| strain | $MIC^a$ (µg/mL) | | | | | | | |
|---|---|---|---|---|---|---|---|---|
| | Closantel | Rafoxanide | 5i | 6a | 7b | 8 | metronidazole | vancomycin |
| *C. sporogenes* ATCC 15579 | 1 | 1 | >32 | 8 | 16 | 4 | 0.25 | 2 |
| *C. clostridioforme* ATCC 25537 | 4 | 1 | >32 | 4 | 16 | 4 | 0.06 | 0.5 |

TABLE 4-continued

In vitro activity against select anaerobic bacteria

| strain | MIC$^a$ (μg/mL) | | | | | | | |
|---|---|---|---|---|---|---|---|---|
| | Closantel | Rafoxanide | 5i | 6a | 7b | 8 | metronidazole | vancomycin |
| *B. thetaiotaomicron* ATCC 29148 | >32 | >32 | >32 | >32 | >32 | >32 | 1 | >32 |
| *P. distasonis* ATCC 8503 | 16 | 8 | >32 | 16 | 8 | 4 | 2 | >32 |
| *P. nigrescens* ATCC 33563 | 8 | 8 | >32 | 8 | 4 | 4 | 2 | >32 |

$^a$Performed in duplicate. For clarity, MIC values against Gram-positive and Gram-negative bacteria are shown in blue and red, respectively.

Synthesis and Characterization of Compounds

Closantel (Sigma), rafoxanide (TCI America), niclosamide (Combi-Blocks), oxyclozanide (Sigma), metronidazole (Combi-Blocks), and vancomycin hydrochloride hydrate (Sigma) were used as received.

Compounds 5a-i, 6a-c, 7a-d, 9a-b, 10a-b, 11a-f and 12 were prepared as previously described.[2-4] Compounds 7e-i and 8 were synthesized according to published procedure.[2] Briefly, 3,5-diiodosalicylic acid (or 3,5-dichlorosalicylic acid, 1 eq) was heated to reflux with $SOCl_2$ (5 eq) for 7 h, and thereafter concentrated under reduced pressure. The corresponding acyl chloride product was precipitated with cold hexanes, filtered and air-dried. Coupling with the respective amine (1 eq) was performed in DMF in the presence of DIPEA (3 eq) at rt for 1 h. All salicylanilide products were purified by preparative HPLC. Reagents and solvents were obtained from commercial sources, and reactions were carried out using technique known to those having ordinary skill in the art.

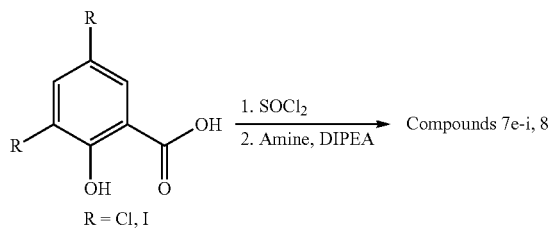

$^1$H and $^{13}$C NMR spectra were recorded on Bruker DRX-600 equipped with a 5 mm DCH cryoprobe. Purity of all tested products were generally >95% as assessed by HPLC.

N-(9H-Fluoren-2-yl)-2-hydroxy-3,5-diiodobenzamide (7e)

Yield: 40%. $^1$H NMR (600 MHz, $CDCl_3$) δ 3.94 (s, 2H), 7.30-7.34 (m, 1H), 7.39 (t, J=7.3 Hz, 1H), 7.44-7.48 (m, 1H), 7.56 (d, J=7.4 Hz, 1H), 7.75-7.81 (m, 2H), 7.81 (d, J=1.8 Hz, 1H), 7.89 (s, 1H), 7.98 (s, 1H), 8.20 (d, J=1.8 Hz, 1H). $^{13}$C NMR (151 MHz, $CDCl_3$) δ 37.2, 80.4, 89.1, 116.9, 118.5, 120.0, 120.3, 120.5, 125.2, 127.0, 127.1, 134.3, 134.8, 139.9, 141.0, 143.4, 144.6, 151.1, 160.5, 166.4. HRMS-ESI (m/z): [M+H]$^+$ calcd for $C_{20}H_{14}I_2NO_2$, 553.9114; found, 553.9110.

N-(2-Chlorophenethyl)-2-hydroxy-3,5-diiodobenzamide (7f)

Yield: 49%. $^1$H NMR (500 MHz, DMSO-d$_6$) δ 2.99 (t, J=7.2 Hz, 2H), 3.54 (q, J=7.0 Hz, 2H), 7.24-7.31 (m, 2H), 7.34 (dd, J=2.1, 7.2 Hz, 1H), 7.44 (dd, J=1.9, 7.3 Hz, 1H), 8.16 (d, J=1.9 Hz, 1H), 8.18 (d, J=1.9 Hz, 1H), 9.26 (t, J=5.6 Hz, 1H). $^{13}$C NMR (151 MHz, DMSO) δ 32.3, 81.4, 88.8, 116.2, 127.4, 128.4, 129.3, 131.2, 133.2, 135.1, 136.4, 149.4, 159.8, 168.1. HRMS-ESI (ml z): [M+H]$^+$ calcd for $C_{15}H_{13}ClI_2NO_2$, 527.8719; found, 527.8706.

N-(3-Chlorophenethyl)-2-hydroxy-3,5-diiodobenzamide (7g)

Yield: 53%. $^1$H NMR (500 MHz, DMSO-d$_6$) δ 2.87 (t, J=7.2 Hz, 2H), 3.53 (q, J=7.0 Hz, 2H), 7.19-7.22 (m, 1H), 7.26-7.29 (m, 1H), 7.30-7.35 (m, 2H), 8.16 (d, J=1.9 Hz, 1H), 8.17 (d, J=1.9 Hz, 1H), 9.22 (t, J=5.5 Hz, 1H). $^{13}$C NMR (151 MHz, DMSO) δ 34.0, 40.5, 81.4, 88.9, 116.2, 126.3, 127.5, 128.6, 130.2, 133.0, 135.1, 141.6, 149.4, 159.8, 168.1. HRMS-ESI (m/z): [M+H]$^+$ calcd for $C_{16}H_{13}ClI_2NO_2$, 527.8719; found, 527.8717.

N-(4-Chlorophenethyl)-2-hydroxy-3,5-diiodobenzamide (7h)

Yield: 51%. $^1$H NMR (500 MHz, DMSO-d$_6$) δ 2.85 (t, J=7.2 Hz, 2H), 3.51 (q, J=7.2 Hz, 2H), 7.27 (d, J=8.5 Hz, 2H), 7.35 (d, J=8.5 Hz, 2H), 8.16 (d, J=1.9 Hz, 1H), 8.18 (d, J=2.0 Hz, 1H), 9.21 (t, J=5.4 Hz, 1H). $^{13}$C NMR (151 MHz, DMSO) δ 33.7, 40.7, 81.4, 88.9, 116.2, 128.3, 130.6, 130.9, 135.1, 138.1, 149.4, 159.8, 168.0. HRMS-ESI (m/z): [M+H]$^+$ calcd for $C_{15}H_{13}ClI_2NO_2$, 527.8719; found, 527.8713.

N-(2,4-Dichlorophenethyl-2-hydroxy-3,5-diiodobenzamide (7i)

Yield: 59%. $^1$H NMR (500 MHz, DMSO-d$_6$) δ 2.97 (t, J=7.0 Hz, 2H), 3.53 (q, J=6.9 Hz, 2H), 7.35-7.39 (m, 2H), 7.60 (d, J=1.1 Hz, 1H), 8.14-8.19 (m, 2H), 9.23 (t, J=5.5 Hz, 1H). $^{13}$C NMR (151 MHz, DMSO) δ 31.8, 81.4, 88.8, 116.2, 127.5, 128.7, 131.9, 132.5, 134.1, 135.1, 135.7, 149.4, 159.8, 168.2. HRMS-ESI (m/z): [M+H]$^+$ calcd for $C_{15}H_{12}Cl_2I_2NO_2$, 561.8329; found, 561.8319.

3,5-Dichloro-N-(4-(4-chlorophenoxy)phenyl)-2-hydroxybenzamide (8)

Yield: 55%. $^1$H NMR (600 MHz, $CDCl_3$) δ 6.96 (d, J=8.8 Hz, 2H), 7.04 (d, J=8.9 Hz, 2H), 7.31 (d, J=8.8 Hz, 2H), 7.50 (d, J=2.3 Hz, 1H), 7.53 (d, J=8.9 Hz, 2H), 7.56 (d, J=2.3 Hz, 1H), 8.02 (s, 1H), 12.16 (s, 1H). $^{13}$C NMR (151 MHz, $CDCl_3$) δ 116.6, 119.6, 120.3, 123.5, 123.7, 124.2, 124.6, 128.8, 130.0, 131.6, 134.3, 154.9, 155.8, 156.0, 166.6. HRMS-ESI (m/z): [M+H]$^+$ calcd for $C_{19}H_{13}Cl_3NO_3$, 407.9955; found, 407.9955.

SYNTHETIC METHODS DOCUMENTS CITED (1) Terada, H.; Goto, S.; Yamamoto, K.; Takeuchi, I.; Hamada, Y.; Miyake, K. *Biochim. Biophys. Acts* 1988, 936, 504.
(2) Gooyit, M.; Tricoche, N.; Lustigman, S.; Janda, K. D. *J. Med. Chem.* 2014, 57, 5792.
(3) Gooyit, M.; Tricoche, N.; Javor, S.; Lustigman, S.; Janda, K. D. *ACS Med. Chem. Lett.* 2015, 6, 339.
(4) Gooyit, M.; Harris, T. L.; Tricoche, N.; Javor, S.; Lustigman, S.; Janda, K. D. *ACS Infect. Dis.* 2015, 1, 198.

What is claimed is:

1. A method of treatment of a *Clostridium difficile* infection in a mammal, comprising administering to the mammal an effective dose of a compound of formula (I)

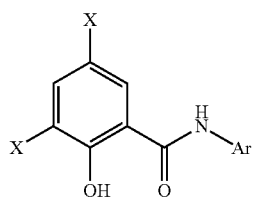
(I)

wherein X is halo or H, provided at least one X is halo, wherein the ring bearing X is optionally further substituted with halo;
wherein Ar is phenethyl, unsubstituted or independently substituted with one or more halo, (C1-C4)alkyl, cyano, or nitro groups.

2. The method of claim 1, wherein X is chloro or iodo.
3. The method of claim 1, wherein Ar is substituted with halo or (C1-C4)alkyl, or both.
4. The method of claim 1, wherein the compound of formula (I) is any one of compounds

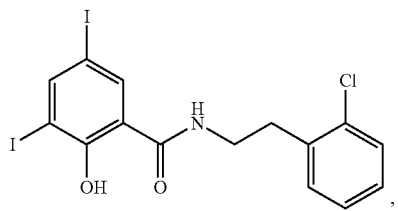
(7f)

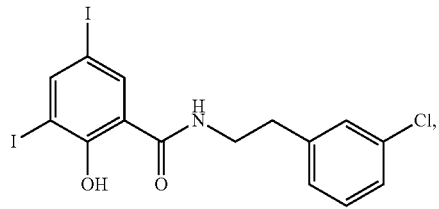
(7g)

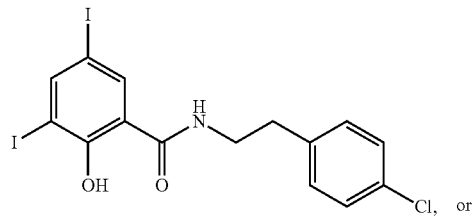
(7h)

, or

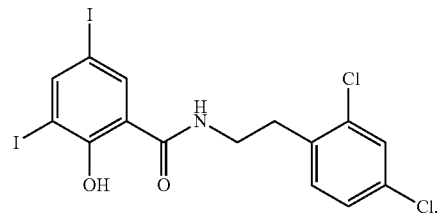
(7i)

* * * * *